United States Patent [19]

Wills

[11] Plant 4,300

[45] Sep. 12, 1978

[54] DOGWOOD TREE

[76] Inventor: Mel Wills, Box 484, 365 Second St., Fairview, Oreg. 97024

[21] Appl. No.: 834,154

[22] Filed: Sep. 16, 1977

[51] Int. Cl. ..... A01H 5/00

[52] U.S. Cl. ..... Plt./51

[58] Field of Search ..... Plt./51

*Primary Examiner*—Robert E. Bagwill

*Attorney, Agent, or Firm*—Klarquist, Sparkman, Campbell, Leigh, Hall & Whinston

[57] ABSTRACT

A limb sport of *Cornus florida rubra* characterized by smaller, more wrinkled leaves which are variegated green and yellow, with rose colorations when immature and deep red to reddish-purple colorations in the autumn.

4 Drawing Figures

The present invention relates to a new and distinct variety of dogwood tree of the species botanically known as *Cornus florida rubra* and commonly called "Pink Dogwood." I discovered my new variety as a limb sport of a *Cornus florida rubra* tree which had been budded onto *Cornus florida* understock and which was growing in a cultivated area of my nursery in Troutdale, Oreg.

While engaged in the routine care of my nursery I was attracted to the limb sport because of the reddish coloration of its leaves. Further examination of these reddish leaves revealed that they were variegated. Close observations of the limb sport and continued observations of progeny thereof, subsequently asexually propagated by me in Troutdale, Oreg. and Fairview, Oreg. by budding, confirmed that the unique leaf coloration of my new variety was the result of a bud sport.

I am, therefore, convinced that my new tree represents a new and improved variety of *Cornus florida rubra* as particularly evidenced by the following unique combination of characteristics, which have proven firmly fixed, are outstanding therein, and which distinguish it from all other varieties of this species:

1. Variegated leaves having a generally centrally oriented sharply defined dark colored area surrounded by a light colored peripheral area, many of such leaves also having sharply defined patches of an intermediate color abutting the dark central area and positioned within the light peripheral area;

2. Newly formed leaves having an initial rose coloration which gradually fades and eventually disappears;

3. Leaves that are smaller and generally more wrinkled than leaves of known varieties of *Cornus florida rubra.*

The accompanying photographs depict colors of the foliage of my new variety as nearly true as is reasonably possible to make the same in a color illustration of this character.

FIG. 1 is a color photograph of the tree of the present invention taken late in June 1977;

FIG. 2, the lower figure in the drawing, is a color photograph of leaves of the tree of my invention taken at the same time as the photograph of FIG. 1 to show leaves of my variety in progressive stages of development;

FIG. 3, located at the right hand side of the drawing above FIG. 2, is a color photograph of leaves of the tree of my invention taken early in November 1976 to show fall colors of its leaves; and FIG. 4, located in the upper right hand corner of the drawing, is a color photograph of leaves of the tree of my invention taken at the same time as the photograph of FIG. 3 to show the effect of shading on the development of fall colors of the leaves.

As previously indicated, the newly formed leaves of my tree are rose colored. Thereafter, as the leaves age, the rose color gradually fades until it is found only at the side edges of the leaves. Eventually this rose color disappears entirely. FIG. 2 depicts this progressive change in color from the younger leaves in the upper rows to the more mature leaves in the lower row.

As the leaves of my variety mature, their variegated coloration becomes more pronounced. In early summer, the leaves have a centrally oriented area of a dark green color and an outer peripheral area of a yellow color. This dark central area is distinctly defined and often terminates at leaf veins. Although varying in size and shape from leaf to leaf, the dark central area in general covers a substantial portion of the leaf and terminates short of the side edge margins of the leaf. Thus, the combination of the dark central area with the light colored peripheral area creates "a leaf within a leaf" effect.

In addition to the dark green central area and yellow area, many of the leaves of my variety also have sharply defined patches of an intermediate green color. These patches usually abut the dark green area and often are positioned within the light peripheral area.

Therefore, the leaves of my tree in early summer typically possess three sharply defined areas of coloration. In addition to these three colors, many of the immature leaves have areas that are rose colored, as explained above.

In the fall, the dark central areas of the leaves darken to a deep purple color. In addition, the yellow peripheral area gradually takes on a red coloration while the intermediate patches progressively turn a red-purple in color. FIG. 3 depicts leaves of my variety in their fall colors. In general, shading of the leaves of my variety, for example by other leaves of the same tree, slows the transition of the leaves to their fall colors. As examples, the leaf at the left of FIG. 3 was taken from an interior shaded portion of a tree of my variety and the lighter colored portion at the right of the other leaf in FIG. 3 was shaded by an adjacent leaf.

As the leaves of the tree of my invention progressively change in coloration, the tree at a particular time will have leaves in different stages of color development. Thus, a tree having leaves which vary strikingly in color is produced.

Unlike the coloration of my new variety, the leaves of known *Cornus florida rubra* trees are green in the spring and darken to a red color in the fall.

In addition to the color differences, the leaves of my new tree are generally smaller and appear more wrinkled than the leaves of known varieties of this species.

The flowers of my new tree, like those of known varieties of this species, are pink. Also, the other physical characteristics of my new variety, insofar as I have been able to observe, appear to be generally typical of the species.

The following is a detailed description of my new variety of *Cornus florida rubra* tree, with color terminology in accordance with the "Royal Horticultural Society Color Charts" (hereinafter R.H.S.), published by the Royal Horticultural Society of London. It is pointed out, however, that the coloration of the leaves as indicated below is only approximate because the coloration varies considerably as the leaves age.

Parentage: A limb sport of a *Cornus florida rubra* tree which had been budded onto *Cornus florida* understock.

Propagation: Holds to distinguishing characteristics through succeeding propagation by budding.

Locality where grown and observed: Troutdale, Oreg. and Fairview, Oreg.

Tree: Upright.

Foliage:

*Shape.*—Ovate to elliptic-ovate.

*Size.*—Mature leaf is typically about 10 cm long and 5 cm broad.

*Apex.*—Accuminate to acute.

*Base.*—Broadly wedge-shaped to rounded.

*Margin.*—Tends to be somewhat wrinkled.

*Color.*—As described above and more specifically: Newly formed leaf — initially a rose color (like RHS plate 53-B). Early summer colors — Central dark area: a dark green color like RHS plate 137-C; Peripheral light area: a yellow color like RHS plate 14-C; Intermediate patches: a green color like RHS plate 146-D. Fall colors — Central dark area: a deep red-purple color not shown in RHS but somewhat darker than plate 183-A; Peripheral light area: a red color like RHS plate 53-B; Intermediate patches: a red-purple color like RHS plate 184-A.

I claim:

1. A new and distinct variety of dogwood tree substantially as herein shown and described, characterized particularly as to novelty by having variegated leaves with a generally centrally oriented sharply defined dark colored area surrounded by a light colored peripheral area, many of such leaves also having sharply defined patches of intermediate coloration.

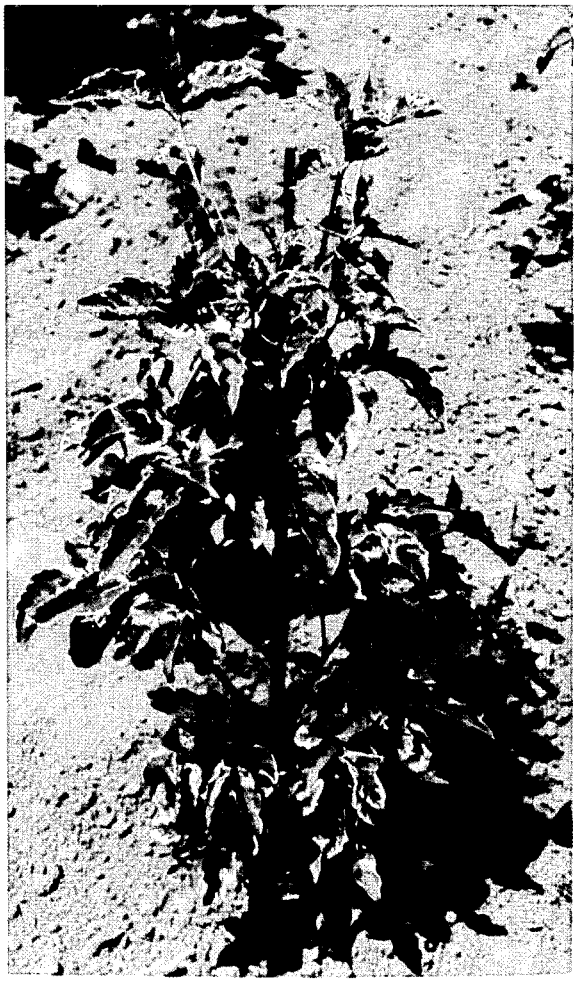
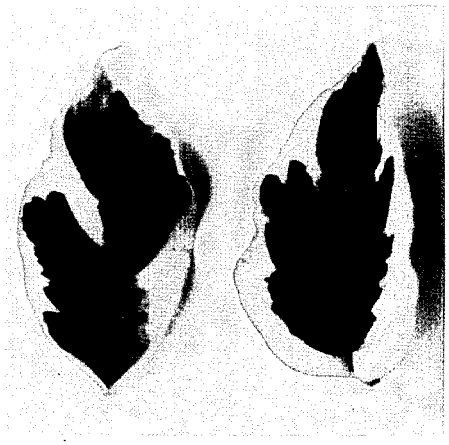
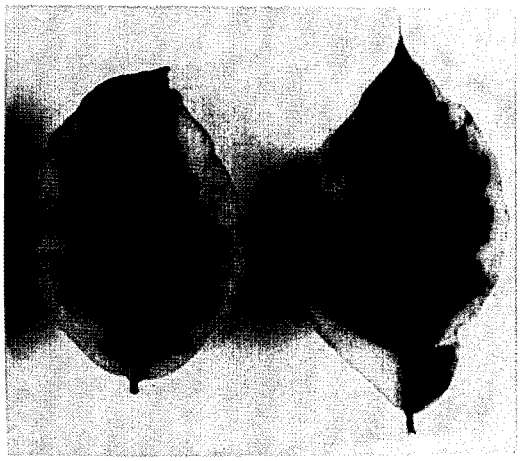
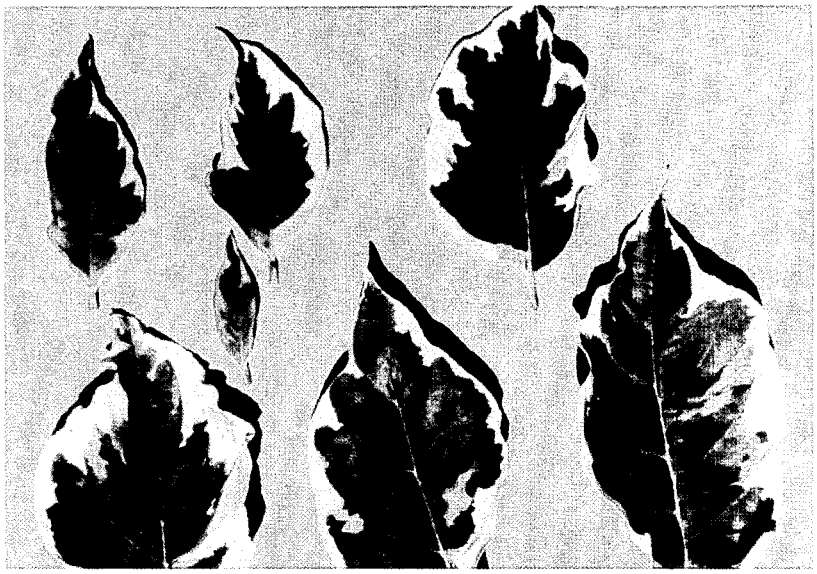

* * * * *